United States Patent [19]

Tokubo et al.

[11] Patent Number: 5,165,915
[45] Date of Patent: Nov. 24, 1992

[54] SPHERICAL CLAY MINERAL POWDER, PROCESS FOR PRODUCTION THEREOF AND COMPOSITION CONTAINING THE SAME

[75] Inventors: Kazuo Tokubo; Michihiro Yamaguchi; Jyunko Suzuki; Toshio Yoshioka; Fujihiro Kanda; Minoru Fukuda; Toshihide Ikeda; Takeshi Kawaura; Yoshiaki Yagita, all of Yokohama, Japan

[73] Assignee: Shiseido Company Ltd., Tokyo, Japan

[21] Appl. No.: 538,595

[22] Filed: Jun. 19, 1990

Related U.S. Application Data

[63] Continuation of Ser. No. 184,549, Mar. 21, 1988, abandoned.

[30] Foreign Application Priority Data

| Jul. 24, 1986 | [JP] | Japan | 61-174578 |
| Aug. 11, 1986 | [JP] | Japan | 61-188333 |
| Aug. 20, 1986 | [JP] | Japan | 61-194493 |
| Aug. 20, 1986 | [JP] | Japan | 61-194494 |
| Sep. 4, 1986 | [JP] | Japan | 61-208624 |
| Sep. 5, 1986 | [JP] | Japan | 61-209160 |
| Sep. 5, 1986 | [JP] | Japan | 61-209161 |

[51] Int. Cl.$^5$ .............. A61K 7/02; A61K 7/021; A61K 7/48; A61K 9/12

[52] U.S. Cl. .................. 424/63; 106/14.5; 424/DIG. 5; 424/47; 424/59; 424/60; 424/61; 424/64; 424/65; 424/67; 424/68; 424/69; 512/4; 514/847

[58] Field of Search .............. 424/63, 59, 47; 514/949

[56] References Cited

U.S. PATENT DOCUMENTS

| 3,439,088 | 4/1969 | Edman | 424/63 |
| 3,998,973 | 12/1976 | Carlson | 514/949 |
| 4,431,673 | 2/1984 | Goldner et al. | 424/63 |
| 4,659,571 | 4/1987 | Laba | 514/949 |
| 4,783,333 | 11/1988 | Mercado et al. | 424/63 |

FOREIGN PATENT DOCUMENTS

| 1230742 | 9/1960 | France | 514/949 |
| 51-41443 | 4/1976 | Japan | 424/63 |
| 0032024 | 3/1977 | Japan | 424/63 |
| 0228406 | 10/1985 | Japan | 424/63 |
| 1065807 | 4/1986 | Japan | 514/949 |
| 1111367 | 5/1986 | Japan | 424/63 |

*Primary Examiner*—Dale R. Ore
*Attorney, Agent, or Firm*—Sprung Horn Kramer & Woods

[57] ABSTRACT

A spherical clay mineral powder or spherical composite powder comprising water-swellable clay mineral with specific surface are of 100 m$^2$/g or more is provided, and the composite powder can contain an organic, inorganic or metal powder, an organic substance soluble in an organic solvent or a water-soluble substance, and these spherical powders can be formulated effectively in, for example, cosmetics.

6 Claims, 5 Drawing Sheets

SPHERICAL CLAY MINERAL POWDER, PROCESS FOR PRODUCTION THEREOF AND COMPOSITION CONTAINING THE SAME

This application is a continuation of application Ser. No. 184,549, filed Mar. 21, 1988, now abandoned.

TECHNICAL FIELD

The present invention relates to a spherical clay mineral powder or spherical composite powder comprising a water-swellable clay mineral with a specific surface area of 100 m$^2$/g or more, a process for production thereof, and a composition containing the same. These spherical clay mineral powders are suitable as a filler in rubbers, plastics, etc., due to their excellent moldability, and as a powder for use in cosmetics and pharmaceuticals, due to their excellent tactility.

The term "specific surface area" as used in the present specification is a BET method value determined from the nitrogen adsorption amount at the liquid nitrogen temperature, and in water-swellable clay mineral, refers to the value corresponding to the outer surface area including the end surfaces, because no nitrogen molecule has penetrated between the layers at the liquid nitrogen temperature.

PRIOR ART

The swelling and gelling characteristics of a water-swellable clay mineral have enabled its use as a dispersing stabilizer for paints, pharmaceuticals, cosmetics and it is also utilized in powder form as a filler for plastics, rubbers, and the like. Particularly when utilized in the powdery form, whether a natural or a synthetic product, it is finally reduced to powder by mechanical pulverization, and therefore, most particles have an indefinite form and thus a poor efficiency when used as a filler, and can be formulated only with difficulty in cosmetics, in which importance form characteristic gives a gritty touch.

On the other hand, powders have surface activities, and thus will frequently cause a deterioration of co-existing components in pharmaceutical, food, cosmetic, paint, etc., systems.

To prevent this problem, a composite powder has been formed by coating the powder surface with another powder by utilizing, for example, a sand mill. However, even in these composite powders, the powder covering the powder surface may also cause deterioration.

Further, it is known in the art that a water-swellable clay mineral undergoes interlayer reaction with organic polar molecules or cationic molecules of alcohol, amine, water-soluble polymer, etc., to form an organic composite clay mineral having a new function. However, when the organic composite clay mineral is taken out in powdery form, generally the steps of filtration or centrifugation are employed and after drying of the precipitate, pulverization with a strong mechanical force, whereby most of the particulate forms obtained exhibit an indefinite form, and therefore, the feeling during use has an extremely gritty touch, and thus the drawback arises that they can be formulated only with difficulty into cosmetics in which importance is attached to tactility, except for a formulation when swollen or when dispersed in an aqueous solvent.

Also, to inhibit an excessive moisture evaporation into the air from the epithelial cells or to strengthen the hydration action to corneum, an emollient agent has been frequently formulated, but this has a drawback of a sticky feeling during use when formulated in a large amount.

An oil-soluble dye, typically a natural dye, involves a problem of light resistance, and the like, and has a drawback in that it may be dissolved into oil when used as a pigment when formulated in a powdery product or that, due to a weak coloration, the powder must be formulated in a large amount, thus raising costs and having a poor useability. Some of the perfumes have a drawback in that the aroma becomes weaker with an elapse of time, and that a uniform mixing can be done only with difficulty when a perfume is given to a product consisting only of powder.

Also, primarily for the purpose of maintaining moisture on the skin, various water-soluble substances, typically polyhydric alcohol, are formulated in cosmetics. However, although many water-soluble substances have an excellent humectant action, they also have a drawback of a sticky feeling during use when formulated in a large amount. Also, a liquid water-soluble substance has a drawback in that it can be formulated in a powdered cosmetic such as pressed powder only with difficulty.

As described above, a water-swellable clay mineral has been used as the dispersing stabilizer for paints, pharmaceuticals, and cosmetics by utilizing its swellability, gelling characteristic, since it has a particularly high stability and good gelling ability, and therefore, is preferable for use in cosmetics, above all in a powder dispersion system or emulsified system product (e.g., eyeliner, mascara, emulsion, cream, nail enamel). Generally speaking, it is formulated in the form of a gel dispersed in an aqueous solvent.

On the other hand, the formulation of the powdery form as such directly into a cosmetic is rarely practiced, but even if formulated directly in the powdery form, due to its indefinite form, a gritty feeling occurs during use, and therefore, it can be formulated only with difficulty into a cosmetic in which importance is attached particularly to the feeling during use.

Accordingly, in the prior art, regarding the use of a water-swellable clay mineral in cosmetics, it has been used as the gelling agent in an aqueous system, an emulsifier in a water-oil system, but there is no case in which it has been used as the powder.

Further, concerning the causes of bad odors derived from living bodies, such as axillary odor, sweat odor, food odor, hair odor, or physiological odor, these are mostly caused by the bacteriolysis of sweat (e.g., Labows and Kligman et al, J. Soc. Cosmet., Vol. 34, p. 193). Many products intended to reduce these bad odors are commercially available, but most of these are formulations comprise sweat inhibitors such as aluminum hydroxychloride, sterilizers such as quaternary ammonium compound, masking agents composed mainly of pleasant odors such as eugenol, or activated charcoal either alone or in combination.

SUMMARY OF THE INVENTION

Accordingly, an object of the present invention is to solve the problems of the prior art as described above, in the making of the water-swellable clay mineral spherical powder, and the like, because the spherical clay mineral powder having an excellent filling efficiency and an excellent feeling during use.

Another object of the present invention is to provide a composite powder which is also stable in various systems by enclosing the surface activity of the desired powder by incorporating one or two or more kinds of organic, inorganic or metallic powder or inorganic sol-like substance in a powder comprising water-swellable clay mineral without impairing the function of the desired powder.

Still another object of the present invention is to provide a composite powder, which is a spherical organic composite clay mineral powder containing a water-swellable clay mineral and an organic substance soluble in an organic solvent and, when the organic substance is an emollient agent, has a moist feeling during use and an excellent emollient effect without stickiness even when formulated in a large amount, or when the organic substance is an oil-soluble dye, has an excellent light resistance and coloration power, or when the organic substance is a perfume, has an excellent safety and slow release property, giving in all cases, a smooth feeling during use due to the spherical shape, and further, can be stably formulated in powdery cosmetics.

Still another object of the present invention is to provide an excellent spherical composite powder which is an organic composite clay mineral comprising a water-swellable clay mineral and a water-soluble substance, having a smooth and moist feeling during use as well as an excellent humectant action, without stickiness even when formulated in a large amount, and further, can be formulated stably in powdery cosmetics.

Still another object of the present invention is to make a water-swellable clay mineral spherical, which can be formulated in a cosmetic, thereby providing a cosmetic having a transparency and good feeling during use, such as slippage, etc.

Still another object of the present invention is to provide a deodorant with a good safety and good useability and having a truly excellent deodorizing effect which persists for a long time, in view of the state of the prior art deodorant of an insufficient deodorizing effect, non-persistency of the effect or unsatisfactory local application, safety and useability.

The spherical clay mineral powder according to the present invention comprises a water-swellable clay mineral with a specific surface area of 100 m$^2$/g or more, and the water-swellable spherical clay mineral powder can be produced by dispersing a water-swellable clay mineral with a specific surface area of 100 m$^2$/g or more in an aqueous dispersion, and then spray drying the dispersion.

According to the present invention, there is also provided a spherical composite powder containing one kind or two kinds or more of organic, inorganic or metallic powder or inorganic sol-like substance in powder comprising a water-swellable clay mineral with a specific surface area of 100 m$^2$/g or more, which composite powder can be prepared by spray drying one kind or two or more kinds of organic, inorganic or metallic powder or inorganic sol-like substance and an aqueous dispersion of the water-swellable clay mineral.

According to the present invention, there is further provided an organic composite clay mineral powder containing a water-swellable clay mineral with a specific surface area of 100 m$^2$/g or more and an organic substance soluble in an organic solvent.

According to the present invention, there is further provided an organic composite clay mineral, powder containing a water-swellable clay mineral with a specific surface area of 100 m$^2$/g or more and a water-soluble substance.

According to the present invention, there is further provided a cosmetic containing a spherical water-swellable clay mineral powder formulated therein, and the cosmetic is smooth and has a good slippage, and can be used for a cosmetic having a higher transparency (smaller shielding property) compared with general extender pigments used in cosmetics.

According to the present invention, there is further provided a deodorant comprising a composite powder comprising a water-swellable clay mineral and powder having a deodorizing activity, and its embodiments are inclusive of deodorants for external use such as an aerosol, roll-on, powder, cream, stick, and for modes such as a lining sheet in shoes and deodorants for domestic use.

BRIEF DESCRIPTION OF THE DRAWINGS

The present invention is described below by referring to the drawings.

PREFERRED EMBODIMENTS FOR PRACTICING THE INVENTION

Figure 1:
FIG. 1 is a scanning electron microscope photograph ($\times 10,000$) showing the crystalline structure of the spherical clay mineral powder according to the present invention obtained in Example 1.

The water-swellable clay mineral to be used in the present invention may include water-swellable clay minerals with a specific surface area of 100 m$^2$/g or more, preferably 150 m$^2$/g or more, particularly synthetic layered silicate minerals such as hectorite or saponite. As such water-swellable clay minerals, for example, commercially available products such as Laponite (Laporte Co.), Smecton SA (Kunimine Kogyo), etc. can be suitably used. In the present specification, "water-swellable" clay mineral means a layered silicate mineral which becomes a uniform gel which is approximately transparent when dispersed in water.

The spherical clay mineral powder according to the present invention can be most simply prepared by the spray drying method according to, for example, the present invention, whereby a spherical powder with regular particle forms and particles sizes can be obtained.

More specifically, it is a method in which a water-swellable clay mineral with a specific surface area of 100 m$^2$/g or more is dispersed in an aqueous medium to be gelled, and then the dispersion is spray dried.

In the preparation of the above gel, it is desirable to control the concentration of the water-swellable clay mineral to not higher than 20% by weight, particularly desirably, 1 to 10% by weight. At a concentration exceeding 20% by weight, the gel viscosity is higher, whereby delivery of the liquid to a spraying nozzle at the time of spray drying is very difficult, and clogging of the nozzle, etc. may occur.

Also, during the preparation of the above gel, preferably stirring is performed until the water-swellable clay mineral is sufficiently dispersed and swollen. In the case of insufficient dispersion and swelling, clogging of the nozzle during spray drying may occur, or in some cases, the spherical clay mineral may become undesirably irregular.

During spray drying, spray drying methods in general such as disc type, pressure nozzle system, 2-fluid nozzle system, etc. can be applied. In each case, the inlet air temperature during spraying can be set at a broad temperature range of about 150° to 300° C. Also, the exhaust temperature may be defined depending on the spray flow rate from the nozzle, etc., but may be around approximately 100° C. Generally, the spherical clay mineral may have a particle size of 2 to 30 $\mu$m. Also, the form of the particle surface becomes uniform and smooth, as the appearance of the above gel is more transparent and has a higher viscosity (for example, in the case of Laponite).

The spherical clay mineral obtained as described above is then calcined, if desired. The calcination temperature, the calcination time and the atmosphere for calcination may be selected depending on the use, but the calcination temperature must not be higher than the temperature at which mutual sintering occurs between the spherical clay minerals. This temperature is about 900° C. or higher. At a calcination temperature range lower than that temperature, a change in crystalline structure by X-ray diffraction measurement may sometimes occur, but this is not a problem if the shape remains spherical. The particle size will not be substantially changed by calcination. By such calcination, the water absorptivity of the spherical powder is reduced and further the water-swellability is lost, thus having a remarkable specific feature that no gel is formed but the spherical shape is maintained even when dispersed in water.

Formulation of the spherical clay mineral according to the present invention into a cosmetic is possible in all concentration ranges, and is generally 0.05% to 50% by weight. In the case of emulsified, dispersed products, a concentration ranging from 0.5% to 5% by weight is general, and in the case of powdery or powder pressed type, a concentration ranging from 0.1% to 30% by weight is general.

In the cosmetic of the present invention, in addition to the above spherical clay, other components generally formulated in cosmetics can be formulated within the qualitative, quantitative ranges which do not impair the present invention. Examples of such components are oil components, waxes, pigments, powders, surfactants, preservatives, dyes, antioxidants, UV-ray absorbers, perfumes, humectants such as polyhydric alcohols, chelating agents, acids, alkalis, water-soluble polymers, oil-soluble polymers, clay minerals.

Specific examples of oil components, waxes, pigments, surfactants are enumerated below.

Waxes and oil components: animal and vegetable oils such as tallow, squalene olive oil, evening primrose oil, rice bran oil, candelilla wax, carnauba wax, mineral oils such as hydrocarbons, fluid paraffins, solid paraffins; ester oils such as isopropyl myristate, pentaerhtritol-tetra-2-ethylhexanoate, silicone oils such as methylphenylsilicone, dimethylsilicone; alcohols such as 2-octyldodecanol, 2-decyltetradecanol, oleyl alcohol, cetyl alcohol; fatty acids such as behenic acid, oleic acid, isostearic acid; and, higher alcohols such as oleyl alcohol, cetanol, stearyl alcohol.

Surfactants: nonionic surfactants, including polyoxyethylene (hereinafter abbreviated as POE)-branched alkyl ethers such as POE-octyldodecyl alcohol, POE-2-decyltetradecyl alcohol; POE-alkyl ethers such as POE-oleyl alcohol ether, POE-cetyl alcohol ether; sorbitan esters such as sorbitan monooleate, sorbitan monoisostearate, sorbitan monolaurate; POE-sorbitan esters such as POE-sorbitan monooleate, POE-sorbitan monoisostearate, POE-sorbitan monolaurate; glycerine fatty acid esters such as glycerine monooleate, glyceryl monostearate, glyceryl monomyristate; POE-glycerine fatty acid esters such as POE-glyceryl monooleate, POE-glyceryl monostearate, POE-glyceryl monomyristate; POE-hardened castor oil fatty acid esters such as POE-hardened castor oil, POE-hardened castor oil isostearate; POE-alkyl aryl ethers such as POE-octyl phenol ether; glycerol ethers such as glycerol monomyristate; POE-glycerol ethers such as POE-glycerol monoisostearate, POE-glycerol monomyristate; polyglycerine fatty acid esters such as diglyceryl monoisostearate, decaglyceryl decastearate, decaglyceryl decaisostearate, diglyceryl diisostearate; anionic surfactants, including salts of higher fatty acids such as myristic acid, stearic acid, palmitic acid, behenic acid, isostearic acid, oleic acid; with potassium, sodium, diethanolamine, triethanolamine, amino acid; the above alkali salts of ether carboxylic acids, salts of N-acylamino acids, salts of N-acylsarcosinic acids, salts of higher alkylsulfonic acids; cationic surfactants, including alkylamine salts, polyamines, aminoalcohol fatty acid organic silicone resins, alkyl quaternary ammonium salts; or amphoteric surfactants.

Pigments: inorganic pigments such as talc, mica, kaolin, calcium carbonate, zinc white, titanium dioxide, red iron oxide, yellow iron oxide, black iron oxide, ultramarine, prussian blue, chromium hydroxide, titanium coated mica, bismuth oxychloride; organic pigments such as crystalline cellulose, nylon powder, polyethylene powder.

The technique for carrying other components in powder comprising a water-swellable clay mineral is known. However, as other components to be carried, only dyes and the like are known, and these are all incorporated as molecules between the clay mineral layers, and not as a solid of one or two or more of the organic, inorganic or metal powders according to the present invention.

Also, in the prior art, when taking out the composite powder comprising a water-swellable mineral and a dye; as the powder from an aqueous solvent, since the step of pulverizing the precipitate dried after the operations of filtration, centrifugation, etc., is employed, a long time is needed for this work. Also, the particle form of the powder obtained tends to become indefinite and having sharp angles, thus involving the drawback that it cannot be formulated in a large amount, particularly in cosmetics in which great importance is attached to the feeling during use.

As the powder to be contained in the powder comprising the water-swellable clay mineral of the present invention, any organic, inorganic or metal powder or inorganic sol-like substance can be used.

Representative examples may include organic powder such as of polyamide resin, polyethylene resin, acrylic resin, polyester resin, fluorine resin and cellulose resin; inorganic powder such as of titanium dioxide, talc, kaolin, hydroxyapatite, zinc white, barium sulfate, magnesium carbonate, calcium carbonate, silica, calcium secondary phosphate, iron oxide, chromium oxide, chromium hydroxide, ultramarine, prussian blue; metallic powder such as aluminum powder, gold powder, silver powder, iron powder, copper powder, zinc powder; and inorganic sol-like substance such as silica sol, alumina sol, titania sol, zirconia sol.

However, the particle size of the above organic, inorganic or metallic powder should be preferably 0.5 $\mu$m or less in average particle diameter, particularly 0.1 $\mu$m or less, since the composite powder constituted of the water-swellable clay mineral and these powders has a particle size of about 2 to 30 $\mu$m. If the size is greater than this, the above powder to be contained within the powder of the water-swellable clay mineral will undesirably appear frequently on the surface of the composite material.

The content of the organic, inorganic or metallic powder or the inorganic sol-like substance in the composite powder comprising the water-swellable clay mineral and one kind or two or more kinds of the organic, inorganic or metallic powder or the inorganic sol-like substance may be 0.1% to 100% by weight of the total amount of the composite powder.

The particle size of the composite powder comprising the water-swellable clay mineral and one kind or two or more kinds of the organic, inorganic or metallic powder or the inorganic sol-like substance is 2 to 30 $\mu$m on an average.

The composite powder may have any desired shape, but particularly when formulated into a product to which the feeling during use is important, such as cosmetics, etc., it should be preferably approximately spherical. To obtain a spherical composite powder, the following preparation process according to the present invention is most preferable.

The process for producing the composite powder of the present invention is described as follows.

First, one kind or two or more kinds of organic, inorganic or metallic powder or inorganic gel-like substance to be contained is dispersed in an aqueous solvent. Here, to enhance dispersibility, various surfactants or dispersing agents such as sodium hexametaphosphate may be added. Next, a water-swellable clay mineral is added to this dispersion to prepare a gel. It is important that one kind or two or more kinds of the above organic, inorganic or metallic powder or inorganic gel-like substance be uniformly dispersed in the gel. Finally, the dispersion thus obtained is spray dried, whereby water jetted out from the nozzle is instantly evaporated to give the composite powder of the present invention. The obtained composite powder is spherical.

The concentration of the water-swellable clay mineral in the above gel preferably is 10% by weight or less. At a concentration exceeding this level, the gel viscosity becomes too high, whereby delivery of the liquid to the spraying nozzle during spray drying is difficult, and clogging of the nozzle or the like is liable to occur.

The content of one kind or two or more kinds of the organic, inorganic or metallic powder may be determined so that the weight in the total weight of the composite powder after drying may be within the above range.

During spray drying, a general spray drying method such as disc type, pressure nozzle system, 2-fluid nozzle system, etc. can be applied. The inlet air temperature during spraying, which also depends on the stability of the one kind or two or more kinds of the organic, inorganic or metallic powder, can be set at a broad temperature range of about 100° to 300° C., because the water-swellable clay mineral is thermally stable up to about 300° C.

The exhaust temperature may differ depending on the spraying flow rate from the nozzle, but may be generally around 100° C.

The spherical clay mineral thus obtained has a particle size of 2 to 30 μm, and exhibits a spherical shape. The particle surface becomes more uniform and smooth as the appearance of the gel prepared is more transparent, and the viscosity of the gel is higher (for example, in the case of Laponite).

The composite powder of the present invention thus obtained has a particle size of about 2 to 30 μm on an average, although this can slightly differ depending on the spray drying conditions.

The spherical composite powder obtained above is then calcined, if desired. The calcination temperature, the calcination time, and the atmosphere for calcination may be selected depending on the use, but the calcination temperature must not be higher than the temperature at which a mutual sintering occurs between spherical clay minerals. This temperature is about 900° C. or higher. At a calcination temperature lower than that temperature, a change in crystalline structure may be sometimes occur, but this is not a problem if the shape remains spherical. The particle size of the spherical composite powder thus obtained is not substantially changed by calcination, but the water absorptivity of the spherical powder is reduced by calcination, and further, the water swellability is lost.

The organic substance soluble in an organic solvent to be used in the present invention is a substance insoluble in water, including specific oil components having an emollient effect, oil-soluble dyes, perfumes, UV-rays absorbers.

Examples of the oil component having the emollient effect, may include isopropyl myristate, myristyl lactate, dipentaerythritol fatty acid ester, glycerine trimyristate, alkylene glycol fatty acid ester.

Examples of the oil-soluble dye may include tar dyes such as red color No. 215, red color No. 218, red color No. 223, red color No. 225, orange color 201, yellow color 204, green color 202, violet color 201, etc., natural dyes such as B-carotene, annatto, sakuro-high yellow, carmic acid, etc.

Examples of perfume may include linalol, linalyl acetate, cinnamic aldehyde, benzyl acetate, citral, cimene, limonene, etc.

Example of the UV-rays absorber may include paraaminobenzoic acid, homomenthyl-N-acetylanthranilate, anilsalicylate, octylsalicylate, 2,4-dihydroxybenzophenone.

The organic composite clay mineral of the present invention is a spherical powder containing the above water-swellable clay mineral and an organic substance soluble in an organic solvent, having a particle size of 2 to 30 μm.

The amount of the water-swellable clay mineral formulated in the total amount of the organic composite clay mineral may be 25% to 99.5% by weight, preferably 50% to 99.9% by weight, and the amount of the organic substance soluble in an organic solvent formulated in the total amount of the organic composite clay mineral may be 0.05% to 75% by weight, preferably 0.1% to 50% by weight.

The organic composite clay mineral of the present invention may be prepared according to any desired process, but the following spray drying process is the simplest and most preferable for obtaining an organic composite clay mineral with a regular spherical shape.

More specifically, in this method the water-swellable clay mineral is dispersed in an aqueous solvent to be gelled, and then the spherical water-swellable clay mineral is obtained by spray drying of the gel.

The concentration of the water-swellable clay mineral in the above gel may be preferably 10% by weight or less. At a concentration higher than that level, the gel viscosity becomes, too high, whereby delivery of the liquid to the spraying nozzle during spraying is difficult, and clogging of the nozzle or the like may be occur. A particularly preferable concentration range is 1% to 10% by weight.

During preparation of the gel, preferably stirring is performed until the water-swellable clay mineral is sufficiently dispersed and swelled. In the case of an insufficient dispersion and swelling, clogging of the nozzle during spray drying may occur, or in some cases, the organic composite clay minerals obtained may become undesirably irregular.

For spray drying, a general spray drying method such as disc type, pressure nozzle system, 2-fluid nozzle system, may be applied.

In all cases, the inlet air temperature during spraying is preferably in the temperature range at which the swellable clay mineral is thermally stable, and may be about 150° to 300° C.

The exhaust temperature may be defined depending on the spray flow rate from the nozzle or the like, but may be around 100° C.

The clay mineral thus obtained is a substantially truly spherical powder having a structure comprising primary particles of water-soluble clay mineral agglomerated, having a particle size of 2 to 30 μm. The form of the particle surface becomes more uniform and smooth as the appearance of the gel previously formed is more transparent and the viscosity is higher (for example, in the case of Laponite).

Next, the spherical water-swellable clay mineral thus obtained is dispersed in an organic solvent containing the above organic substance dissolved therein, and thereafter, the organic solvent is volatilized. The organic solvent to be used may be any general low boiling solvent, as exemplified by methanol, ethanol, chloroform, ether, hexane and the like.

The organic substance dissolved in an organic solvent according to such operations is included as permeated between the layers of spherical water-swellable clay mineral to give a spherical organic composite clay mineral.

The spherical water-swellable clay mineral is not swollen in an organic solvent, and therefore, its shape is not changed. The organic composite clay mineral thus obtained maintains its original shape.

The water-soluble substance to be used in the present invention is any desired water-soluble substance, including muco-polysaccharides such as hyaluronic acid, chondroitin sulfuric acid A, chondroitin sulfuric acid B, chondroitin sulfuric acid C, heparin sulfuric acid, heparin keratin sulfuric acid; natural water-soluble polymers, for example, vegetable polymers such as gum arabic, gum tragacanth, galactane, guar gum, carob gum, karaya gum, caragheenan, pectin, agar, quince seed (marmelo), algae colloid (brown algae extract), starch (rice, corn, potato, wheat); microorganism polymers such as xanthan gum, dextran, succinoglucan, pullulane, semi-synthetic water-soluble polymers, for example, starch polymers such as carboxymethyl starch, methlhydroxypropyl starch, cellulose polymers such as methylcellulose, nitrocellulose, ethylcellulose, methylhydroxypropyl cellulose, hydroxyethyl cellulose, sodium cellulose nitrate, hydroxypropyl cellulose, sodium carboxymethyl cellulose (CMC), crystalline cellulose, cellulose powder; alginic acid polymers such as sodium alginate, alginic acid propylene glycol ester; synthetic water-soluble polymers, for example, vinyl polymers such as polyvinyl alcohol, polyvinylmethyl ether, polyvinyl pyrrolidone, carboxyvinyl polymer (Carbopol); polyoxyethylene (hereinafter called POE) polymers such as polyethylene glycols 20,000, 40,000,000, 600,000; copolymers such as POE-polyoxypropylene (hereinafter called POP), acrylic polymers such as sodium polyacrylate, polyethylacrylate, polyacrylamide, etc., polyethyleneimine, cationic polymer; polyhydric alcohols, for example, dihydric alcohols such as ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol, etc., trihydric alcohols such as glycerine, trimethylolpropane, 1,2,6-hexanetriol; tetrahydric alcohols such as pentaerytritol; pentahydric alcohols such as xylitol, hexahydric alcohols such as sorbitol, mannitol; polyhydric alcohol polymers such as diethylene glycol, dipropylene glycol, triethylene glycol, polypropylene glycol, tetraethylene glycol, diglycerine, polyethylene glycol, triglycerine, tetraglycerine, polyglycerine; dihydric alcohol alkyl ethers such as ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether; dihydric alcohol alkyl ethers such as diethylene glycol monomethyl ether, diethylene glycol monoethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ether, dipropylene glycol butyl ether; dihydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate; sugar alcohols such as sorbitol, maltitol, maltrose, mannitol, sucrose, erythritol, glucose, fructose, starch sugar, maltose, xylitose, starch sugar reduced alcohol; POE tetrahydrofuryl alcohol, POP butyl ether, POP, POE butyl ether, tripolyoxypropylene glycerine ether, POP glycerine ether, POP glycerine ether phosphoric acid, POP POE pentaerythritol ether; water-soluble proteins such as collagen, casein, albumin, gelatin; quaternary ammonium salts such as stearyl trimethylammonium chloride, lauryl trimethylammonium chloride, distearyl dimethylammonium chloride; phospholipids such as lecithin, hydrogenated lecithin; organic amines such as monoethanolamine, diethanolamine, triethanolamine, morpholine, triisopropanolamine, 2-amino-2-methyl-1,3-propanediol, 2-amino-2-methyl-1-propanol; amino acids such as glycine, alanine, valine, leucine, isoleucine, serine, threonine, phenylalanine, thyrosine, tryptophane, cystine, cysteine, methionine, proline, hydroxyproline, neutral amino acids such as L-Dopa; acidic amino acids such as aspartic acid, glutamic acid, asparagine, glutamine; basic amino acids such as alaginine, hystidine, lysine; and also amino acid derivatives such as sodium acylsarcosinate (sodium lauroylsarcosinate), acylglutamic acid salt, acyl-$\beta$-alanine sodium, glutathione, pyrrolidonecarboxylic acid.

Among them, polyhydric alcohols and mucopolysaccharides are particularly desirable.

In practicing the present invention, one or two or more kinds are selected as desired from these water-soluble substances.

The organic composite clay mineral of the present invention is a spherical powder containing the above water-swellable clay mineral and a water-soluble substance, and having a particle size of 2 to 30 $\mu$m.

The amount of the water-swellable clay mineral formulated in the total amount of the organic composite clay mineral may be 25% to 99.5% by weight, preferably 50% to 99.9% by weight, and the amount of the water-soluble substance formulated in the total amount of the organic composite clay mineral may be 0.05% to 75% by weight, preferably 0.1% to 50% by weight.

The organic composite clay mineral of the present invention may be prepared according to any desired process, but the following spray drying process is the simplest and most preferable for obtaining an organic composite clay mineral with a regular spherical shape.

More specifically, it is a method in which the above water-soluble substance is dissolved in an aqueous solvent, and further, the above water-swellable clay mineral is dispersed therein to be gelled, and then the gel can be spray dried to obtain an organic composite mineral containing a water-swellable clay mineral and a water-soluble substance.

The concentration of the water-swellable clay mineral in the above gel containing the water-soluble substance and the water-swellable mineral may be preferably 20% by weight or less. At a concentration higher than that level, the gel viscosity becomes too high, whereby delivery of the liquid to the spraying nozzle during spraying is difficult, and also clogging of the nozzle may occur. A particularly preferable concentration range is 1% to 10% by weight.

The concentration of the water-soluble substance in the above gel may be preferably 0.001% to 5% by weight. At a concentration more than this range, a water-soluble substance which cannot be included within the organic composite clay mineral also appears, whereby the amount of the water-soluble substance adsorbed on the organic composite clay mineral surface may be increased to give an undesirable sticky feeling during use or effect powdering of the water-soluble substance alone.

During preparation of the gel, preferably stirring is performed until the water-swellable clay mineral is sufficiently dispersed and swollen. In the case of an insufficient dispersion and swelling, clogging of the nozzle during spray drying may occur, or in some cases, the organic composite clay minerals obtained may become undesirably irregular.

For spray drying, a general spray drying method such as disc type, pressure nozzle system, 2-fluid nozzle system, etc., may be applied.

In all cases, the inlet air temperature during spraying is preferably in the temperature range where the swellable clay mineral is thermally stable, and may be about 100° to 200° C.

The exhaust temperature may be defined depending on the spray flow rate from the nozzle or the like, but may be around 100° C.

The clay mineral thus obtained is a substantially truly spherical powder having a structure comprising primary particles of water-soluble clay mineral agglomerated, having a particle size of 2 to 30 $\mu$m. The form of the particle surface becomes more uniform and smooth, as the appearance of the gel previously formed is more transparent and the viscosity is higher (for example, in the case of Laponite).

In the preparation of the organic composite clay mineral according to the process of the present invention, when a polyhydric alcohol or the like is selected as the water-soluble substance, the polyhydric alcohol is included between the layers of the water-swellable clay mineral. This can be confirmed by expansion of the longer interplaner spacing in X-ray diffraction.

When a muco-polysaccharide, is selected as the water-soluble substance, this will-not penetrate between the layers of clay mineral, but is included with the organic composite clay mineral in the form adsorbed on the primary particle surface of the water-swellable clay mineral.

On the other hand, when the water-soluble substance is soluble in an organic solvent other than water, as another method for preparation of such a spherical organic composite clay mineral, a method is known in which spherical clay mineral is prepared and, thereafter, a water-soluble substance is permeated therethrough. More specifically, by spray drying a water-dispersed gel Only of the water-swellable clay mineral, a spherical clay mineral containing no water-soluble substance is obtained. By dispersing this in an organic solvent containing a water-soluble substance previously dissolved therein, and thereafter volatilizing the organic solvent, the water-soluble substance will be included in the spherical clay mineral dispersed. The spherical organic composite clay mineral thus prepared becomes entirely the same powder as the powder obtained by spray drying of a water-dispersed gel previously containing the water-soluble substance and the water-swellable clay mineral dispersed therein. In general, the organic solvent used at this time may be a low boiling solvent. For example, methanol, ethanol, acetone, chloroform, ether, and hexane can be utilized. As the water-soluble substance soluble in organic solvent, polyhydric alcohols, quaternary ammonium salts, etc. may be included.

The amount of the spherical organic clay mineral formulated in cosmetic may be as desired depending on the form of the cosmetic, ranging generally from 0.1% to 80% by weight. In the case of an emulsified, dispersed system, it is generally 0.1% to 50% by weight, and is generally 0.1% to 70% by weight in the case of powdery or powdery pressed type products.

In the cosmetic of the present invention, in addition to the above spherical organic clay mineral, other components generally formulated in cosmetics can be formulated within the qualitative and quantitative ranges which do not impair the effect of the present invention. Such components may include oil components, waxes, pigments, powders, surfactants, preservatives, dyes, antioxidants, UV-rays absorbers, perfumes, humectants such as polyhydric alcohols, chelating agents, acids, alkalis, water-soluble polymers, oil-soluble polymers, clay minerals.

On the other hand, the powder having a deodorizing activity to be used in the present invention may include metal oxides such as zinc oxide, magnesium oxide, calcium oxide, hydroxyapatite, activated charcoal, zeolite, metal phthalocyanine, glycine metal complex, particularly preferably, zinc oxide.

In the present invention, any desired one kind or two or more kinds from among these can be selected to be used.

The deodorant of the present invention contains a composite powder comprising the above water-swellable clay mineral and the above powder has a deodorizing activity. This composite powder may be preferably in the state in which the powder having a deodorizing activity is embedded internally in the water-swellable clay mineral. In the composite powder in such state, the structure of the composite powder has a multitude of fine pores in the form in which primary particles of the water-swellable clay mineral are gathered together, and therefore, bad odor components which are gaseous are partially trapped in fine pores, a part thereof penetrating into the inner portion of the powder to be deodorized through the reaction with the powder having a deodorizing activity in the inner portion of the powder. Also, in such composite powder, most of the powder having a deodorizing activity exists in the inner portion of the composite powder, and therefore, the powder having a deodorizing activity will not react with other components of the deodorant, and thus a specific feature is found in that the powder having a deodorizing activity can be stably formulated in the product.

Such a composite powder may be specifically prepared by dispersing the powder having a deodorizing activity and the water-swellable clay mineral in an aqueous solvent to prepare a gel containing the powder having a deodorizing activity well dispersed therein, and then drying the gel.

During preparation of the gel, to improve the dispersion of the powder having a deodorizing activity, an activator or a dispersing agent such as sodium hexametaphosphate also may be added.

As the method for drying the gel, there may be included drying by applying heat, freeze drying, spray drying, or the like, of which spray drying is particularly preferred. By spray drying of the gel, the aqueous solvent from the droplets of the aqueous solvent jetted out from the nozzle is rapidly evaporated to give a composite powder. The composite powder thus obtained is spherical and about 2 to 30 $\mu$m, and therefore, the deodorant has the specific feature of being useable with an extremely good slippage in the roll-on, powder, cream, stick type, without clogging from the nozzle in the aerosol type.

The constitutional ratio of the water-swellable clay mineral to the powder having a deodorizing activity can be freely changed depending on the product form and is not particularly limited, but preferably the weight ratio of the powder having a deodorizing activity based on the water-swellable clay mineral is 2% to 60%. With a ratio less than 2%, the deodorizing effect may not be exhibited, and with a ratio exceeding 60%, the powder having a deodorizing activity may appear frequently on the composite powder surface, whereby the merit of composite formation may be lost.

The particle size of the composite powder may be preferably about 2 to 30 $\mu$m in average diameter, with the average particle size of the powder having a deodorizing activity being desirably 0.01 to 0.5 $\mu$m, preferably 0.1 $\mu$m or less.

When the composite powder is to be prepared by drying the gel of the water-swellable clay mineral and the gel of the powder having a deodorizing activity, the composition of the gel may be preferably prepared to a concentration of 0.5% to 10% by weight of the water-swellable clay mineral. At a concentration exceeding 10% by weight, the gel viscosity is too high, whereby delivery of the liquid to the spraying nozzle during spray drying becomes difficult, and clogging of the nozzle, etc. is liable to occur.

During spray drying, a general spray drying method such as disc type, pressure nozzle system, or 2-fluid nozzle system may be applied.

In all cases, the inlet air temperature, which may also depend on the stability of the powder having deodorizing activity, can be set at a wide temperature range of 100° to 300° C., because the water-swellable clay mineral is thermally stable up to 300° C. The exhaust temperature is limited depending on the spray flow rate from the nozzle, but may be generally around 100° C.

When the composite powder is prepared by drying the gel of the water-swellable clay mineral and the gel of the powder having a deodorizing activity, the form of the particle surface becomes more uniform and smooth, as the appearance of the gel previously prepared is more transparent and higher in viscosity (for example, in the case of Laponite).

The deodorant comprising the composite powder according to the present invention has an excellent deodorizing effect, and may be contained in a deodorant for external use such as an aerosol, roll-on, powder, cream, stick, or deodorants in the form of a base lining for shoes and domestic uses in an amount of 0.1% to 100% by weight. With an amount less than 0.1% by weight, the deodorizing effect can be exhibited only with difficulty.

In the composite powder according to the present invention, any desired component known in the art can be formulated into the above essential components. Also, together with said composite powder, it is possible to formulate any component known in the art in the deodorant for external use such as an aerosol, roll-on, powder, cream, stick, or base lining of shoes and deodorants for domestic use.

Examples of such components to be formulated may include oils and fats such as avocado oil, almond oil, olive oil, grape seed oil, sesame oil, sasanqua oil, safflower oil, soybean oil, camellia oil, corn oil, rapeseed oil, persic oil, castor oil, sunflower oil, cottonseed oil, peanut oil, cacao oil, palm oil, coconut oil, tallow, fish fat, hardened oil, turtle oil, pig oil, mink oil, yolk oil; waxes such as whale wax, shellac, beeswax, lanolin, liquid lanolin, carunauba wax, canderilla wax; hydrocarbons such as fluid paraffin, fluid polyisobutylene, squalene, pristane, petrolatum, paraffin, ceresin; fatty acids such as succinic acid, tartaric acid, citric acid, undecylenic acid, lauric acid, myristic acid, palmitic acid, stearic acid, isostearic acid, oleic acid, linoleic acid, ricinoleic acid, behenic acid; alcohols such as ethanol, isopropanol, lauryl alcohol, cetanol, 2-hexaldecanol, stearyl alcohol, isostearyl alcohol, oleyl alcohol, lanolin alcohol; polyhydric alcohols such as ethylene glycol, diethylene glycol monoethyl ether, triethylene glycol, polyethylene glycol, propylene glycol, 1,3-butylene glycol, glycerine, batyl alcohol; sugars such as glucose, sucrose, lactose, xylitol, sorbitol, mannitol, maltitol; esters such as diisopropyl adipate, hexyldecyl isostearate, cetyl isooctanoate, oleyl oleate, decyl oleate, lanolin acetate, butyl stearate, isopropyl myristate, diethyl phthalate, hexyl laurate; metal soaps such as aluminum stearate, magnesium stearate, zinc stearate; natural water-soluble polymeric compounds such as gum arabic, sodium alginate, casein, caragheenan, karaya gum, agar, quince seed, gelatin, dextrin, starch, tragacanth, pectin; semi-synthetic polymeric compounds such as alginic acid propylene glycol, ethyl cellulose, crystalline cellulose, methylcellulose; synthetic polymeric compounds such as carboxyvinyl polymer, polyvinyl methyl ether, methoxyethylene maleic anhydride copolymer; surfactants such as dialkylsulfosuccinates, alkylallylsulfonates, higher alcohol sulfuric acid ester salts, phosphoric acid ester salts; preservatives such as ethyl paraoxybenzoate, methyl paraoxybenzoate, vitamins such as vitamin A, vitamin D, vitamin E, vitamin K; hormones such as estradiol, ethynylestradiol, cortisone; organic dyes such as red color No. 2, blue color No. 1, red color 202, yellow color 201, green color 204, violet color 201; inorganic dyes such as aluminum powder, talc, kaolin, bentonite, mica, mica titanium, red iron oxide, caramine, etc.; UV-ray absorbers such as urocanic acid, cinoxate; antiphlogistic agents such as allantoin, aloe powder, guayzulene; propellants such as Freon 11, Freon 12, Freon 21, Freon 22, Freon 113, Freon 114, Freon C318, methyl chloride, methylene chloride, isobutane, carbon dioxide; and purified water.

Other additives which can be optionally formulated in the deodorant according to the present invention may include, for example, sweat inhibitors such as aluminum hydroxychloride, aluminum chloride, aluminum sulfate, basic aluminum bromide, aluminum phenolsulfonic acid, tannic acid, aluminum naphthalenesulfonic acid, basic aluminum iodide, sterilizers such as 3,4,4-trichlorocarbanilide (TCC), benzalkonium chloride, benzethonium chloride, alkyltrimethylammonium chloride, resorcin, phenol, sorbic acid, salicylic acid, hexachlorophene, masking agents such as musk, scatol, lemone oil, lavender oil, jasmine, benzoin, benzyl acetate, menthol.

The spherical clay mineral of the present invention can be an excellent filler with a high molding efficiency in plastics, rubber, etc. since it is spherical, and excellent as a filler for liquid chromatography. Also, when formulated in cosmetics, a cosmetic having an extremely good slippage without a sandy feeling during use can be provided.

According to the present invention, one kind or two or more kinds of organic, inorganic or metallic powder or inorganic sol-like substance can be also formulated in all bases without reaction with other co-existing components in the system to provide a stable product. Also, as the shape is made more regularly spherical, the powder is suitable as a filler and has a particularly good filling efficiency. Also, the powder has specific features such that when used in paints, the workability and dispersibility are good, and that the useability is good when used in cosmetics.

The spherical organic composite clay mineral is spherical, and therefore, when formulated in cosmetics, gives a smooth and moist feeling during use with an extremely good slippage without a gritty feeling. Also, when the organic substance contained is an oil component having the emollient effect, it is not sticky at all even though having the emollient effect for the skin, having an excellent resistance and coloration power in the case of oil-soluble dye, an excellent stability and slow releasability in the case of a perfume, and further, capable of formulating these substances in any powdered cosmetic.

When a humectant is included as the water-soluble substance, the powder exhibits an excellent humectant action for skin, without stickiness, and further, can stably formulate a water-soluble substance in powdered cosmetics.

The deodorant comprising the composite powder of the present invention as the effective ingredient has an excellent and persistent deodorizing effect due to the embedding of the powder having a deodorizing activity, and since the powder having a deodorizing activity will not react with other components, the product is not deteriorated, and further, has specific features in that it has an excellent feeling during use with a good slippage and a good safety.

EXAMPLES

The present invention is described in more detail below by referring to Examples, but of course, the scope of the present invention is not limited to these Examples.

EXAMPLE 1

Laponite XLG (specific surface area: 330 m$^2$/g) was dispersed in 1,000 ml of water while stirring, and the obtained gel was spray dried by a disc spray drying tester at a disc rotational number of 20,000 rpm, an inlet air temperature of about 200° C. and an exhaust temperature of 110° C. As a result, 24 g of spherical powder of 2 to 30 μm was obtained.

FIG. 1 shows a scanning electron microscope photograph of this product.

EXAMPLE 2

An amount of 10 g of spherical Laponite obtained in Example 1 was added to 100 g of polyvinyl chloride powder, and further, tetrahydrofuran was added as the solvent. After stirring, a sheet was prepared, and heated at 80° C. to evaporate tetrahydrofuran, whereby a vinyl chloride sheet was prepared.

COMPARATIVE EXAMPLE 1

A vinyl chloride sheet was obtained in the same manner as in Example 2 except for using the commercial product of Laponite XLG which is indefinite in shape as such.

For example 2 and Comparative Example 1, measurements were conducted by a differential scanning calorimeter to obtain the results of a glass transition temperature of 70° C. for Comparative Example 1 and 78° C. for Example 2. This is because the shape of the powder of Example 2 is spherical, and therefore has a good filling efficiency, whereby the glass transition temperature was elevated.

When the tensile strength was determined for Example 2 and Comparative Example 1, it was 150 kg/cm$^2$ in the case of Comparative Example 1, while 185 kg/cm$^2$ in the case of Example 2. Thus, it was found that the resin composition formulated with the spherical powder of the present invention is a resin composition having an excellent strength.

EXAMPLE 3

A powdery foundation formulated with the spherical powder obtained in Example 1 was trial-produced according to the following recipe. The numerical values are in % by weight.

| | |
|---|---|
| Spherical powder of Example 1 | 10.0 |
| Talc | 20.0 |
| Mica | 52.5 |
| Iron oxide red | 1.0 |
| Iron oxide yellow | 0.5 |
| Iron oxide black | 0.5 |
| Titanium oxide | 5.0 |
| Fluid paraffin | 5.0 |
| Lanolin | 5.0 |
| Ethyl paraben | 0.3 |
| Perfume | 0.2 |

Preparation method

Powders were charged in a Henschel mixer, uniformly stirred and the remaining components then added and uniformly mixed. The mixture was pulverized by an atomizer and molded in a midplate to obtain a powdery foundation.

COMPARATIVE EXAMPLE 2

A powdery foundation was obtained in the same manner as in Example 3 except for using the commercially available Laponite XLG which is indefinite in shape as such.

For Example 3 and Comparative Example 2, use tests were conducted by a panel of 20 members. Organoleptic evaluation was performed according to the following 5 ranks of 1 to 5.

1. gritty and bad
2. gritty and slightly bad
3. common
4. slightly good slippage
5. good slippage and good useability The average score of Comparative Example 2 was 1.9, and the average score of Example 3 was 4.5. Thus, the spherical powder according to the present invention was found to have an extremely good useability when formulated in a foundation.

EXAMPLE 4

An amount of 30 g of Laponite XLG was dispersed while stirring in 1,000 ml of water. The gel obtained was spray dried by a disc spray drying tester at a disc rotational number of 20,000 rpm, an inlet air temperature of 200° C. and an exhaust temperature of about 100° C., whereby 24 g of 2 to 30 μm spherical powder was obtained. The spherical powder was calcined at 600° C. for 2 hours.

Before calcination, when the powder is dispersed in water, it is disintegrated in shape and gelled, but the calcined powder is not disintegrated in shape but maintains its shape even when dispersed in water.

EXAMPLE 5

An amount of 10 g of the calcined spherical Laponite obtained in Example 4 was added to 100 g of polyvinyl chloride powder, and further tetrahydrofuran was added as the solvent. After the mixture was stirred well, a sheet was prepared and heated at 80° C. to evaporate tetrahydrofuran and prepare a vinyl chloride sheet.

COMPARATIVE EXAMPLE 3

A vinyl chloride sheet was obtained in the same manner as in Example 5 except for using the commercial product of Laponite XLG which is indefinite in shape as such.

For example 5 and Comparative Example 3, measurements were conducted by a differential scanning calorimeter to obtain the results of a glass transition temperature of 70° C. for Comparative Example 1 and 78° C. for Example 2. This is because the shape of powder of Example 2 is spherical, and therefore has a good filling efficiency, whereby the glass transition temperature was elevated.

When the tensile strength was determined for Example 5 and Comparative Example 3, it was 150 kg/cm$^2$ in the case of Comparative Example 1, and 185 kg/cm$^2$ in the case of Example 2. Thus, it has been found that the resin composition formulated with the spherical powder of the present invention is a resin composition having an excellent strength.

EXAMPLE 6

A powdery foundation formulated with the spherical powder obtained in Example 4 was trial-produced according to the following recipe. The numerical values are in % by weight.

| | |
|---|---|
| Spherical powder of Example 4 | 10.0 |
| Talc | 20.0 |
| Mica | 52.5 |
| Iron oxide red | 1.0 |
| Iron oxide yellow | 0.5 |
| Iron oxide black | 0.5 |
| Titanium oxide | 5.0 |
| Fluid paraffin | 5.0 |
| Lanolin | 5.0 |
| Ethyl paraben | 0.3 |
| Perfume | 0.2 |

Preparation method:

Powders were charged in a Henschel mixer, uniformly stirred and the remaining components then added and uniformly mixed. The mixture was pulverized by an atomizer and molded in a midplate to obtain a powdery foundation.

COMPARATIVE EXAMPLE 4

A powdery foundation was obtained in the same manner as in Example 3 except for using the commercially available Laponite XLG which is indefinite in shape as such.

For Example 3 and Comparative Example 2, use tests were conducted by a panel of 20 members.

The average score of Comparative Example 4 was 1.9, and the average score of Example 6 was 4.5. Thus, the spherical powder according to the present invention was found to have an extremely good useability when formulated in a foundation.

EXAMPLE 7

In 1,000 ml of water was dissolved 0.5 g of sodium hexametaphosphate, and further 10 g of fine particulate titanium dioxide with particle sizes of 0.1 μm or less and an average particle size of 0.03 μm (fine particular titanium dioxide Titanium P-25: Degusa Co.) was dispersed by use of a Disper. In the dispersion was dispersed 30 g of a water-swellable clay mineral (specific surface area: 330 m²/g) (Laponite XLG; produced by Laporte Co.) to effect gellation. The gel obtained was spray dried by a disc spray drying tester (disc rotational number 20,000 rpm, at an inlet air temperature of about 180° C., and an exhaust temperature of about 110° C.) to obtain 32 g of spherical composite powder of 2 to 15 μm.

Figure 2:
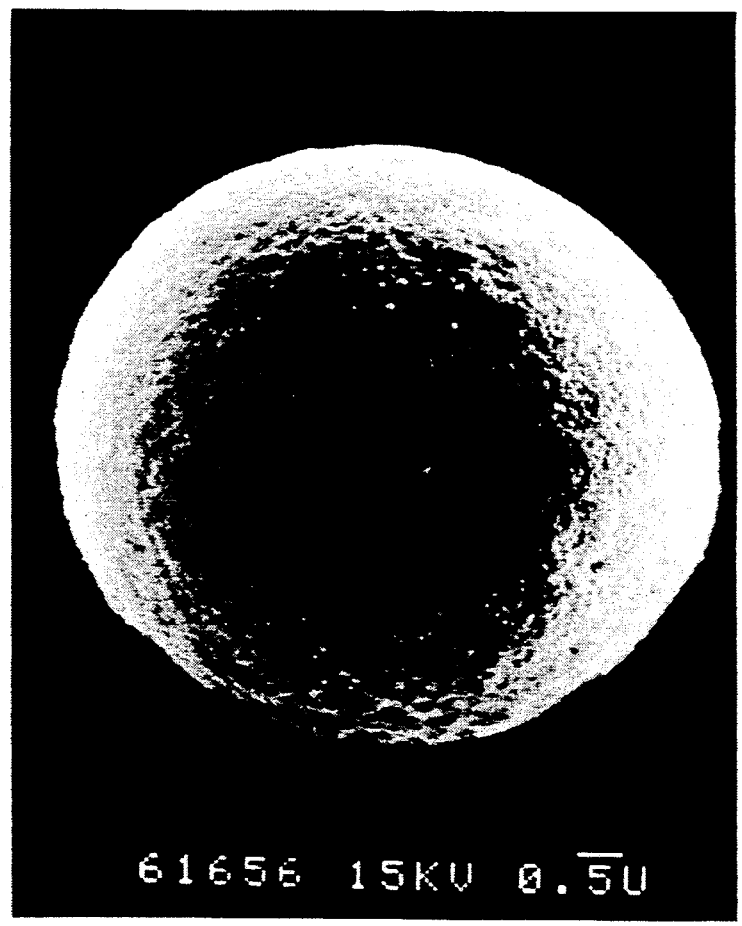
FIG. 2 is a scanning electron microscope photograph showing the crystalline structure of the spherical composite powder of the present invention containing 25% by weight of fine particulate titanium dioxide obtained in Example 7.

FIG. 2 shows a scanning electron microscope photograph of the composite powder. It can be seen that it exhibits a truely spherical shape.

When the true spherical composite powder was analyzed by an energy dispersion type X-ray analyzer, the existence of titanium can be recognized at any site, whereby it could b understood that fine particulate titanium dioxide is uniformly embedded in the spherical composite powder.

TEST EXAMPLE 1

The spherical composite powder obtained in Example 7 was dispersed at 10% by weight in castor oil, kneaded thoroughly on three rollers and then applied on a quartz plate by an applicator to a thickness of 5 μm, followed by measurement of the amount of UV-rays absorbed.

COMPARATIVE TEST EXAMPLE 1

The fine particulate titanium dioxide not applied with the composite powder formation of the present invention (fine particulate titanium dioxide P-25; Degusa Co.) was dispersed at 2.5% (the same as the amount of particulate titanium dioxide as in Test Example 1) in castor oil, and the amount of UV-rays absorbed was measured as in Test Example 1.

Figure 3:
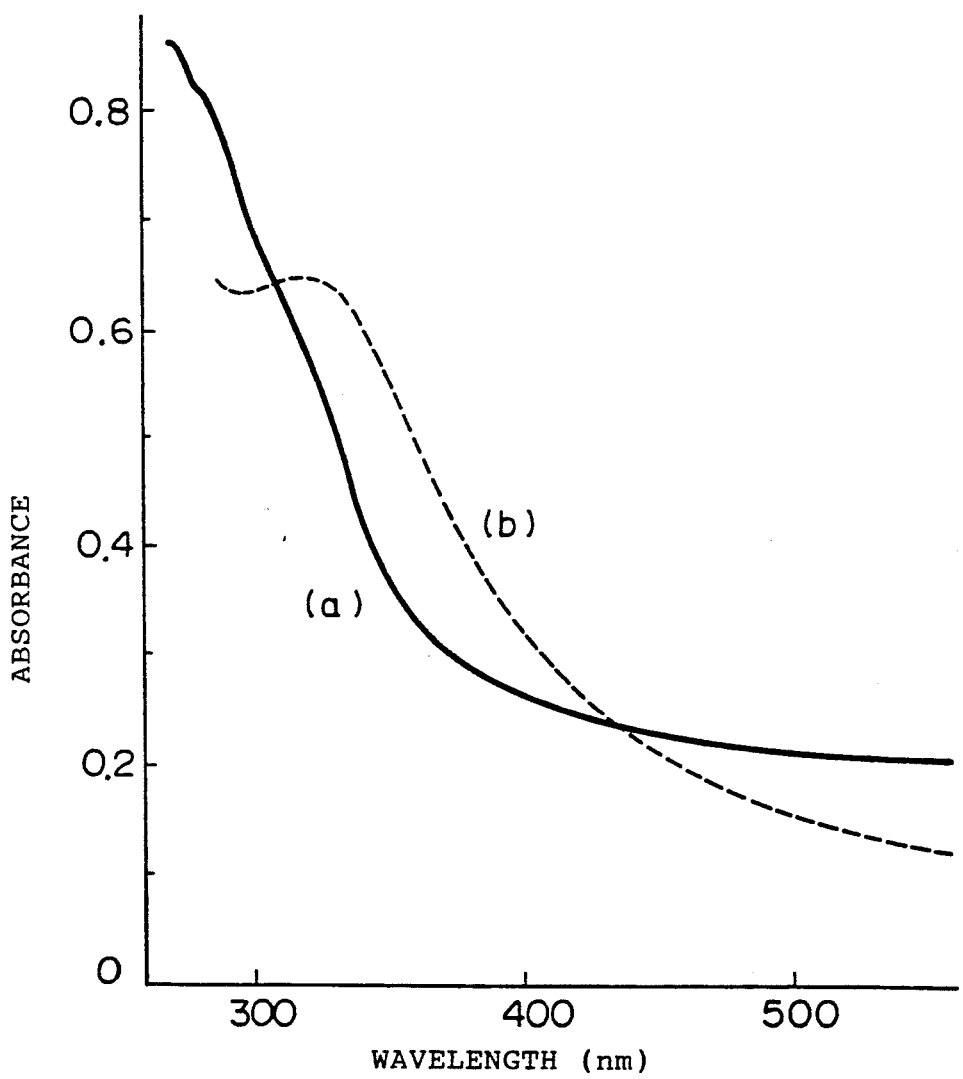
FIG. 3 shows UV-rays absorption curves of the composite powder of the present invention dispersed in castor oil (containing fine particulate titanium dioxide) and fine particulate titanium dioxide alone dispersed similarly in castor oil (curve (a): the composite powder of the present invention, curve (b): fine particulate titanium dioxide alone)

Powders of Test Example 1 and Comparative Example 1 gave the UV-rays absorbance results shown by the curves in FIG. 3.

In either Test Example 1 and Comparative Example 1, the same extent of UV-rays absorbance is exhibited in the UV-rays region of 290 to 320 nm where UV-rays red spot occurs. Thus, it can be understood that the spherical composite powder including the fine particulate titanium oxide has the same UV-rays protecting ability as the fine particulate titanium dioxide alone.

TEST EXAMPLE 2

The spherical composite powder obtained in Test Example 1 was dispersed at 50% by weight in castor oil, and the degree of odor denaturation of castor oil was measured.

COMPARATIVE TEST EXAMPLE 2

The fine particulate titanium dioxide not applied with the composite powder formation of the present invention (fine particulate titanium dioxide P-25; Degusa Co.) was dispersed at 2.5% (the same as the amount of particulate titanium dioxide as in Test Example 1) in castor oil, and the degree of odor denaturation was measured.

The castor oil dispersions of Test Example 2 and Comparative Test Example 2 were stored in a 50° C. thermostat tank, and organoleptic evaluation was conducted for the degree of odor denaturation after 2 weeks.

The results are shown in Table 1. It can be seen that the spherical composite powder of the present invention remarkably inhibits the generation of odor denaturation by a deterioration of the castor oil. This is because most of the surface active sites of the fine particulate titanium dioxide, which brings about deterioration and odor denaturation of castor oil, were enclosed internally within the composite powder by composite powder formation according to the present invention, thereby not coming in contact with the castor oil which is the dispersing medium.

TABLE 1

|  | Degree of odor denaturation at 50° C., after 2 weeks |
|---|---|
| Test Example 2 | substantially no odor denaturation |
| Comparative Test Example 2 | remarkably rancid odor |

EXAMPLE 8

The spherical composite powder obtained in Example 7 was strained through a 200 mesh sieve to obtain a spherical composite powder with particle sizes of 2 to 30 μm.

COMPARATIVE EXAMPLE 5

An amount of 30 parts of Laponite XLG and 10 parts of fine particulate titanium dioxide (P-25; produced by Degusa Co.) were thoroughly mixed to obtain a powdery mixture of both.

Dynamic frictional coefficients of the powders obtained in Example 8 and Comparative Example 5 were measured to obtained the results in Table 2.

For the measurement of the dynamic frictional coefficient, a powder friction tester (Journal of Society of Powder Engineering vol. 21, No. 9, p. 565, 1984) was used, and a double-side tacky tape was plastered on an iron plate placed horizontally, a sample was placed thereon, then a load (5–70 g/cm²) was applied on an attachment made of aluminum, and the shear stress when the attachment was moved right and left at a speed of 10 mm/sec. was measured, and the dynamic frictional coefficient was determined from the relationship between the load and the shear stress.

TABLE 2

|  | Dynamic frictional coefficient |
|---|---|
| Example 8 | 0.32 |
| Comparative Example 5 | 0.60 |

As apparent from Table 2, the spherical composite powder of the present invention can be seen to be spherical composite powder with a good slippage with a smaller frictional coefficient, compared with the simple powdery mixture of Comparative Example 5.

EXAMPLE 9

In 1,000 ml of water, 10 g of aluminum powder with sizes of 0.1 μm or less and an average particle size of 0.08 μm was dispersed. Further, 30 g of Laponite XLG was dispersed to effect gelation. The gel was spray dried as in Example 7 to obtain 32 g of spherical composite powder containing the aluminum resin.

The composite powder was confirmed by scanning electron microscope observation that it is truly spherical and contains aluminum powder embedded extremely uniformly in the powder.

EXAMPLE 10

In 1,000 ml of water was dissolved 0.5 g of sodium hexametaphosphate, and further 10 g of fine particulate titanium dioxide with sizes of 0.1 μm or less and an average particle size of 0.03 μm (fine particulate titanium dioxide P-25; Degusa Co.) was dispersed by a Disper. In the dispersion was dispersed 30 g of a water-swellable clay mineral (Laponite XLG; produced by Laporte Co.) to effect gelation, and the gel obtained was spray dried by a disc spray drying tester (disc rotational number 20,000 rpm, inlet air temperature 180° C., an exhaust temperature about 110° C.) to obtain 32 g of spherical composite powder of 2 to 15 μm. Further, the spherical powder was calcined at 600° C. for 2 hours.

Before calcination, when the powder is dispersed in water, it is disintegrated in shape to be gelled, and the calcined powder is not integrated in shape but maintains its shape even when dispersed in water. Also, when the truly spherical composite powder was analyzed by an energy dispersion type X-ray analyzer, the existence of titanium was recognized at any site, whereby it was understood that fine particulate titanium dioxide is uniformly embedded in the spherical composite powder.

TEST EXAMPLE 3

The spherical composite powder obtained in Example 10 dispersed at 10% by weight in castor oil, kneaded thoroughly on three rollers and then applied on a quartz plate by an applicator to a thickness of 5 μm, followed by measurement of the amount of UV-rays absorbed.

COMPARATIVE TEST EXAMPLE 3

The fine particulate titanium dioxide not applied with the composite powder formation of the present invention (fine particulate titanium dioxide P-25; Degusa Co.) was dispersed at 2.5% (the same as the amount of particulate titanium dioxide as in Test Example 1) in castor oil, and the amount of UV-rays absorbed was measured as in Test Example 2.

In either Test Example 3 and Comparative Example 3, the same extent of UV-rays absorbance is exhibited in the UV-rays region of 290 to 320 nm where UV-rays red spot occurs. Thus, it can be understood that the spherical composite powder including the fine particulate titanium oxide has the same UV-rays protecting ability as the fine particulate titanium dioxide alone.

TEST EXAMPLE 4

The spherical composite powder obtained in Test Example 1 was dispersed at 50% by weight in castor oil, and the degree of odor denaturation of castor oil was measured.

COMPARATIVE TEST EXAMPLE 4

The fine particulate titanium dioxide not applied with the composite powder formation of the present invention (fine particulate titanium dioxide P-25; Degusa Co.) was dispersed at 2.5% (the same as the amount of particulate titanium dioxide as in Test Example 2) in castor oil, and the degree of odor denaturation was measured.

The castor oil dispersions of Test Example 4 and Comparative Test Example 4 were stored in a 50° C. thermostat tank, and an organoleptic evaluation was conducted for the degree of odor denaturation after 2 weeks.

The results are shown in Table 3. It can be seen that the spherical composite powder of the present invention remarkably inhibits the generation of odor denaturation by deterioration of the castor oil. This is because most of the surface active sites of the fine particulate titanium dioxide, which brings about deterioration and odor denaturation of castor oil, were enclosed internally within the composite powder by composite powder formation according to the present invention, thereby not coming into contact with the castor oil which is the dispersing medium.

TABLE 3

|  | Degree of odor denaturation at 50° C., after 2 weeks |
| --- | --- |
| Test Example 4 | substantially no odor denaturation |
| Comparative Test Example 4 | remarkably rancid odor |

EXAMPLE 11

The spherical composite powder obtained in Example 10 was strained through a 200 mesh sieve to obtain a spherical composite powder with particle sizes of 2 to 30 μm.

COMPARATIVE EXAMPLE 6

An amount of 30 parts of Laponite XLG and 10 parts of fine particulate titanium dioxide (P-25; produced by Degusa Co.) were thoroughly mixed to obtain a powdery mixture of both.

The dynamic frictional coefficients of the powders obtained in Example 8 and Comparative Example 5 were measured to obtain the results in Table 4.

For measurement of the dynamic frictional coefficient, a powder friction tester (Journal of Society of Powder Engineering vol. 21, No. 9, p. 565, 1984) was used, and a double-side tacky tape was plastered on an iron plate placed horizontally, a sample was placed thereon, then a load (5-70 g/cm$^2$) was applied on an attachment made of aluminum, the shear stress when the attachment was moved right and left at a speed of 10 mm/sec. was measured, and the dynamic frictional coefficient was determined from the relationship between the load and the shear stress.

TABLE 4

|  | Dynamic frictional coefficient |
| --- | --- |
| Example 11 | 0.32 |
| Comparative Example 6 | 0.60 |

As apparent from Table 4, the spherical composite powder of the present invention can be seen to be a spherical composite powder with a good slippage with a smaller frictional coefficient, compared with the simple powdery mixture of Comparative Example 6.

EXAMPLE 12

In 1,000 ml of water was dispersed 10 g of aluminum powder with sizes of 0.1 μm or less and an average particle diameter of 0.08 μm. Further, 30 g of Laponite XLG was dispersed to effect gelation. The gel was spray dried as in Example 10 to obtain 32 g of a spherical composite powder containing aluminum powder. Further, the spherical powder was calcined at 600° C. for 2 hours. The composite powder was confirmed by a scanning electron microscope or EDX measurement to be truly spherical and contain the aluminum powder extremely uniformly dispersed in the powder.

EXAMPLE 13

Figure 4:
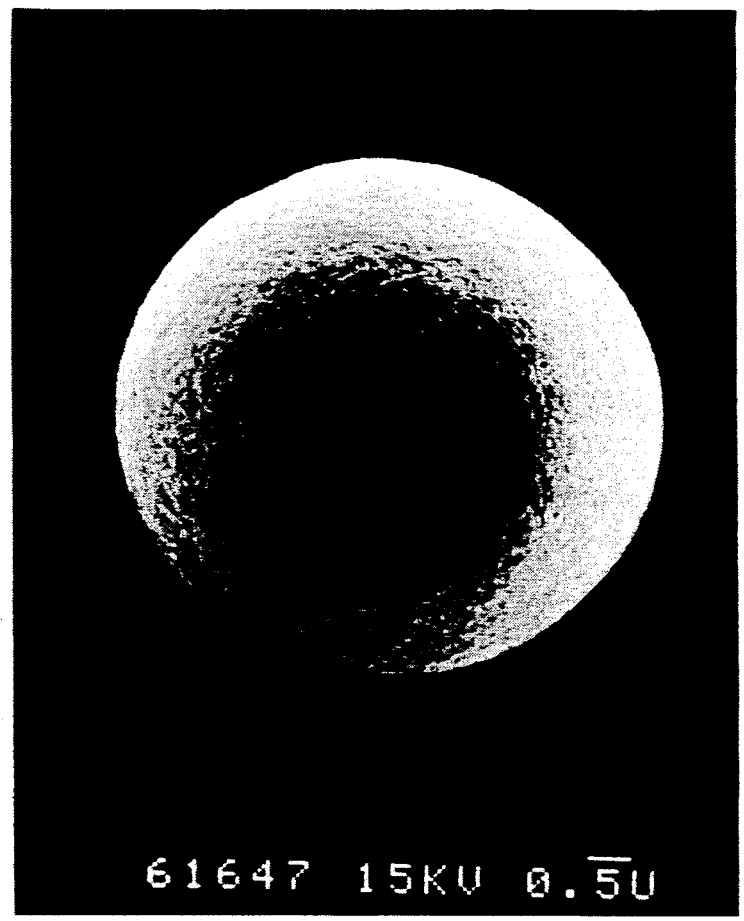
FIG. 4 is a scanning electron microscope photograph showing the spherical composite powder of the present invention containing the perfume component citral obtained in Example 13; and, FIG. 5 is a scanning electron microscope photograph showing the composite powder obtained in Example 26.
Figure 5:
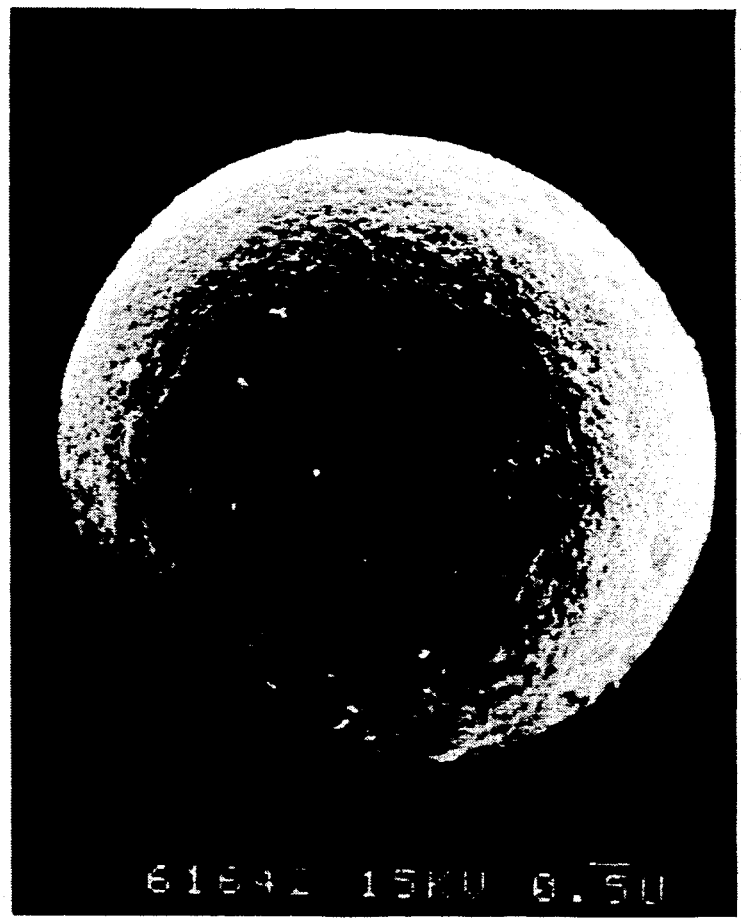

In 1,000 ml of water was dispersed 30 g of Laponite XLG while stirring. The gel obtained was spray dried by a disc spraying drying tester at a disc rotational number of 20,000 rpm, an inlet air temperature of about 180° C. and an exhaust temperature of about 110° C. to obtain 32 g of spherical powder of 2 to 20 μm. To a solution of 5 g of citral, which is the perfume component previously dissolved in 100 ml of ether, was dispersed 20 g of the spherical powder, and the mixture was stirred at room temperature, whereby ether was volatilized and finally only the powder remained. FIG. 4 shows a scanning electron microscope photograph of the powder, from which it can be understood to be spherical. When the interlayer distance was determined by X-ray diffraction, it was found to be expanded by about 4 Å, compared with the case when containing no organic substance, whereby it was confirmed that citral was contained between the layers. The powder, when left to stand in the air, was found to maintain the perfume for a longer term, compared with citral itself.

EXAMPLE 14

To a solution containing 5 g of glycerine trioleate as the emollient agent previously dissolved in 100 ml of hexane was dispersed 20 g of the spherical Laponite including nothing obtained similarly as in the former half of Example 13, and the mixture was stirred at room temperature, whereby hexane was volatilized with time and finally only the powder remained. The powder was found to maintain the spherical shape. By using untreated Laponite and the spherical Laponite including nothing and the spherical Laponite including glycerine trioleate as the emollient agent, foundations were trial-produced according to the formulated amounts shown below.

| | |
|---|---|
| Treated or untreated Laponite | 10.0 |
| Talc | 20.0 |
| Mica | 52.5 |
| Iron oxide red | 1.0 |
| Iron oxide yellow | 0.5 |
| Iron oxide black | 0.5 |
| Titanium oxide | 5.0 |
| Fluid paraffin | 5.0 |
| Lanolin | 5.0 |
| Ethyl paraben | 0.3 |
| Perfume | 0.2 |

Preparation method:
Powders were respectively charged in a Henschel mixer, stirred uniformly and the remaining components then added and uniformly mixed. The mixture was pulverized by an atomizer and molded in a midplate to obtain a powdery foundation.

The results of the trial use tests of these foundations made by a panel of 20 members are shown in Table 5.

Organoleptic evaluation was performed according to the five ranks of 1 to 5 shown below.
1. bad
2. slightly bad
3. common
4. slightly good
5. good.

The results are shown by average scores as follows:
◎ 4.5–5.0
○ 3.5–4.4
Δ 2.5–3.4
x 1.5–2.4

TABLE 5

| Laponite formulated | Slippage when coated | Moistness when coated |
|---|---|---|
| Untreated product | x | Δ |
| Spherical Laponite including glycerine trioleate | ◎ | ○ |
| Laponite including nothing | ◎ | Δ |

EXAMPLE 15

In 1,000 ml of water was dissolved 10 g of glycerine, and further, 30 g of Laponite XLG was dispersed while stirring in the solution. The gel obtained was spray dried by a disc spray drying tester at a disc rotational number of 20,000 rpm, an inlet air temperature of about 180° C. and an exhaust temperature of about 110° C. to obtain 32 g of spherical powder of 2 to 30 μm.

The powder was found to include 25% by weight of glycerine between layers, and the interlayer distance was found by X-ray diffraction to be expanded by about 4 Å.

EXAMPLE 16

In 1,000 ml of water were dissolved 10 g of glycerine and sodium hyaluronate, and further, 30 g of Laponite XLG was dispersed while stirring in the solution. The gel obtained was spray dried as in Example 15 to obtain 32 g of a spherical powder with entirely the same appearance as in Example 15.

COMPARATIVE EXAMPLE 7

In 1,000 ml of water was dispersed 10 g of Laponite while stirring. The gel obtained was spray dried as in Example 16 to obtain 32 g of a spherical powder with entirely the same appearance as in Example 16.

EXAMPLE 17

To a solution of 5 g of glycerine previously dissolved in 100 ml of ethanol, 15 g of the powder obtained in Comparative Example 7 was dispersed, and ethanol was evaporated on a hot water bath. The powder thus obtained remained spherical, and was also found by X-ray to be expanded in the interlayer distance by about 4 Å, similar to the powder obtained in Example 15, whereby it was confirmed that glycerine was contained between the layers.

EXAMPLE 18

Powdery Foundation

By using the untreated Laponite and spherical powders of Example 15 and Comparative Example 7, foundations were trial-produced according to the following formulated amounts (numerical values are in % by weight).

| | |
|---|---|
| Treated or untreated Laponite | 10.0 |
| Talc | 20.0 |
| Mica | 52.5 |
| Iron oxide red | 1.0 |
| Iron oxide yellow | 0.5 |
| Iron oxide black | 0.5 |
| Titanium oxide | 5.0 |
| Fluid paraffin | 5.0 |
| Lanolin | 5.0 |
| Ethyl paraben | 0.3 |
| Perfume | 0.2 |

Preparation method

Powders were respectively charged in a Henschel mixer, stirred uniformly and the remaining components then added and uniformly mixed. The mixture was pulverized by an atomizer and molded in a midplate to obtain a powdery foundation.

The results of the trial use tests of these foundations made by a panel of 20 members are shown in Table 6.

Organoleptic evaluation was performed according to the five ranks of 1 to 5 shown below.
1. bad
2. slightly bad
3. common
4. slightly good
5. good.

The results are shown by average scores as follows:
- ⊚ 5-5.0
- ○ 3.5-4.4
- △ 2.5-3.4
- x 1.5-2.4

TABLE 6

| Laponite formulated | Slippage when coated | Moistness when coated |
|---|---|---|
| Untreated product | x | △ |
| Example 15 | ⊚ | ⊚ |
| Comparative Example 7 | ⊚ | △ |

EXAMPLE 19

Lipstick

A lipstick was trial-produced by using the spherical powder of Example 16 according to the following formulated amounts (numerical values are in % by weight).

| | |
|---|---|
| Spherical powder of Preparation Example 3 | 5 |
| Polyethylene wax | 8 |
| Ceresin wax | 5 |
| Castor oil | 35 |
| Stearyl triglyceride | 30 |
| Fluid paraffin | 16 |
| Iron oxide red | 0.5 |
| Red color No. 204 | 0.5 |
| Perfume | q.s. |

Preparation method

Waxes and oil components were charged in a kettle and melted by heating at 90° C. Further, pigments, perfume and spherical powder were added, and mixed by heating at 85° C. After degassing under a reduced pressure, the mixture was filled in a container, followed by solidification by cooling to obtain a lipstick.

The lipstick obtained was found to smoothly spread and according to the evaluation method as in Example 1, rated ⊚ in both good slippage and moistness.

EXAMPLE 20

Table 7 shows a list of spherical clay minerals prepared according to various conditions.

Further, by using the powder No. 1 in Table 7 and Laponite XLG not in spherical shape (indefinite shape as purchased from Laporte Co.), powdery foundations were prepared and the qualities thereof were measured.

The results are shown in Table 9 (Table 8 shows the recipe trial-produced).

TABLE 7

| | List of Spherical Clay Minerals | | | | | |
|---|---|---|---|---|---|---|
| No. | Water-swellable clay mineral | Dispersed conc. % | Spray drying inlet temp. | Spray drying outlet temp. | Yield g | Particle size |
| 1 | *-1 Laponite XLG 30 g | 3 | 230° C. | 110° C. | 24 | 2–15 μm |
| 2 | *-1 Laponite CP 30 g | 3 | 200° C. | 100° C. | 21 | 2–15 μm |
| 3 | *-2 Smecton SA 30 g | 4 | 200° C. | 100° C. | 23 | 2–15 μm |

*-1 produced by Laporte Co., U.K.
*-2 produced by Kunimine Kogyo Co.

(Preparation method) No. 1 (No. 2 and No. 3 also following No. 1)

Laponite XLG, 30 g, was dispersed while stirring in one liter of water. The gel obtained was spray dried by a disc spray dryer at a disc rotational number of 20,000 rpm, an inlet air temperature of 200° C. and an exhaust temperature of 110° C. to obtain 24 g of a spherical powder of 2 to 10 μm.

TABLE 8

| Powdery Foundation Recipe | |
|---|---|
| Laponite XLG | 10.0 |
| Talc | 20.0 |
| Mica | 52.5 |
| Iron oxide red | 1.0 |
| Iron oxide yellow | 0.5 |
| Iron oxide black | 0.5 |
| Titanium oxide | 5.0 |
| Fluid paraffin | 5.0 |
| Lanolin | 5.0 |
| Ethyl paraben | 0.3 |
| Perfume | 0.2 |
| Total | 100.0 |

Preparation method

Powders were respectively charged in a Henschel mixer, uniformly mixed and the remaining components then added and uniformly mixed. The mixture was pulverized by an atomizer and molded in a midplate to obtain a powdery foundation.

TABLE 9

| Quality Characteristics of Powdery Foundation | | |
|---|---|---|
| Laponite XLG formulated | Spherical (No. 1) | Amorphous |
| Transparent feeling *-1 | o | Δ |
| Useability *-2 (smoothness) | o (4.5) | x (1.9) |

*-1 and *-2 use test results by a panel of 20 members (transparent feeling) organoleptic evaluation of coated color. In the recipe of Table 2, evaluation when the judgement is in the case of using talc in place of Laponite XLG is marked x.

(useability) evaluated according to the following 5 ranks:
1. gritty and bad
2. slightly gritty
3. common
4. slightly good slippage
5. good slippage and smooth The numerals in Table 9 are average scores of a panel of 20 members.

From the results in Table 9, it can be understood that the powdery foundation formulated with the spherical clay mineral has an excellent transparency and a good slippage.

EXAMPLE 21 AND COMPARATIVE EXAMPLE 8

Lipstick

| | Example 21 | Comparative Example 8 |
|---|---|---|
| Polyethylene wax | 3 | 3 |
| Ceresin wax | 7 | 7 |
| Carnauba wax | 2 | 2 |
| Candelilla wax | 5 | 5 |
| Fluid paraffin | 25 | 25 |
| Castor oil | 15 | 15 |
| Di-2-heptylundecanoic acid glycerine | 20 | 20 |
| Olive oil | 11 | 11 |
| Red iron oxide | 0.2 | 0.2 |
| Red color No. 20 | 1.8 | 1.8 |
| Mica | — | 10 |
| Spherical clay mineral *-1 | 10 | — |

*-1 Spherical clay mineral No. 2 in Table 7

Preparation method

Oil components and waxes were melted by heating at 85° to 95° C., and powders were added and dispersed therein. The mixture was immediately degassed under a reduced pressure, transferred into a predetermined container, and solidified by cooling to obtain a lipstick.

Example 21 was found to be a lipstick with an extremely light spread, with the score by the use test in Table 2 being 4.2, and finished with a transparent look. On the other hand, Comparative Example 8 was slightly powdery with a heavy spread, and the score of useability was 2.1.

EXAMPLE 22

Rouge

| | |
|---|---|
| Talc | 30 |
| Mica | 25 |
| Titanium oxide | 3 |
| Titanium coated mica | 5.5 |
| Red color No. 202 | 0.5 |
| Spherical clay mineral *-1 | 20 |
| Sorbitan diisostearate | 1 |
| Squalene | 7 |
| Methylpolysiloxane | 8 |

*-1 spherical clay mineral of No. 3 in Table 7

Preparation method

Pigments were mixed, and other components were added by melting with heating, followed by mixing and pulverization. This was molded in a midplate to obtain a press-shaped rouge.

Example 22 was found to be a rouge with an extremely good spread and finished with a transparent look without a powdery feeling.

EXAMPLE 23

Table 10 shows a list of spherical organic clay minerals prepared under various conditions.

Further, by using the powder of No. 1 in Table 10 and Laponite XLG not in spherical shape (amorphous as purchased from Laporte Co.), powdery foundations were prepared and their quality characteristics were measured.

The results are shown in Table 12 (Table 11 is the recipe).

TABLE 10

| List of Spherical Organic Clay Minerals | | | | | |
|---|---|---|---|---|---|
| No. | Water-swellable clay mineral | Water-soluble substance | Spray drying inlet temp. | Spray drying outlet temp. | Particle size |
| 1 | *-1 Laponite XLG 30 g | Glycerine 10 g | 200° C. | 100° C. | 3–15 μm |
| 2 | *-1 Laponite CP 30 g | Maltitol 10 g | 210° C. | 100° C. | 3–15 |
| 3 | *-2 Smecton SA 30 g | Glycerine 8 g | 200° C. | 100° C. | 4–20 |

*-1 produced by Laporte Co., U.K.
*-2 produced by Kunimine Kogyo Co (Preparation method) No. 1 (No. 2 and No. 3 also follow No. 1)

In one liter of water was dissolved 10 g of glycerine, and 30 g of Laponite XLG was dispersed therein while stirring. The gel obtained was spray dried by a disc spray drying tester at a disc rotational number of 2,000 rpm, an inlet air temperature of 180° C. and an exhaust temperature of about 110° C. to obtain 32 g of spherical powder of 3 to 15 μm. The powder was found to include 25% by weight of glycerine between the layers, and the interlayer distance was found by X-ray diffraction to be 15.5 Å, as expanded by about 4 Å as compared with the starting material Laponite XLG.

Alternative method

In one liter of water was dispersed 30 g of Laponite XLG while stirring. The gel obtained was spray dried by a disc spray drying tester at a disc rotational number of 2,000 rpm, an inlet air temperature of 180° C. and an exhaust temperature of about 110° C. to obtain 28 g of spherical powder of 3 to 15 μm. In a solution of 5 g of glycerine previously dissolved in 100 ml of ethanol was dispersed 15 g of the spherical powder, and the ethanol was evaporated on a hot water bath. The powder thus obtained maintained its original shape, and the interlayer distance was found by X-ray diffraction to be expanded by about 4 Å in exactly the same manner as in the powder obtained in the (Preparation method) No. 1. Thus, glycerine was confirmed to be contained between the layers.

TABLE 11

| Powdery Foundation Recipe | |
| --- | --- |
| Laponite XLG | 10.0 |
| Talc | 20.0 |
| Mica | 52.5 |
| Iron oxide red | 1.0 |
| Iron oxide yellow | 0.5 |
| Iron oxide black | 0.5 |
| Titanium oxide | 5.0 |
| Fluid paraffin | 5.0 |
| Lanolin | 5.0 |
| Ethyl paraben | 0.3 |
| Perfume | 0.2 |

Preparation method

Powders were respectively charged into a Henschel mixer, uniformly stirred and the remaining components then added and uniformly mixed. The mixture was pulverized by an atomizer and molded in a midplate to obtain a powdery foundation.

TABLE 12

| Quality Characteristics of Powdery Foundation | | |
| --- | --- | --- |
| Laponite XLG formulated: | Spherical (No. 1) | Amorphous |
| Moistness *-1 | o | x |
| Smoothness *-2 | o | x |
| | (4.5) | (1.9) |

*-1 and *-2 use test results by a panel of 20 members (Moistness): evaluated according to the following 5 ranks
1. dry
2. slightly dry
3. common
4. slightly moist
5. moist (Smoothness): evaluated according to the following 5 ranks
1. gritty
2. slightly gritty
3. common
4. slightly good slippage
5 good slippage and smooth The numerals in Table 12 are average scores of a panel of 20 members.

From Table 12, it can be understood that the powdery foundation according to the present invention has a good slippage and excellent humectant property.

EXAMPLE 24 AND COMPARATIVE EXAMPLE 9

Lipstick

| | Example 24 | Comparative Example 9 |
| --- | --- | --- |
| Polyethylene wax | 3 | 3 |
| Ceresin wax | 7 | 7 |
| Carnauba wax | 2 | 2 |
| Candelilla wax | 5 | 5 |
| Fluid paraffin | 25 | 25 |
| Castor oil | 15 | 15 |
| Di-2-heptylundecanoic acid glycerine | 20 | 20 |
| Olive oil | 11 | 11 |
| Red iron oxide | 0.2 | 0.2 |
| Red color No. 202 | 1.8 | 1.8 |
| Mica | — | 10 |
| Spherical organic clay mineral *-1 | 10 | — |
| Total | 100.0 | 100.0 |

Preparation method

Oil components and waxes were melted by heating at 85°–95° C., and pigments were added and dispersed therein. The mixture was immediately degassed, transferred into a predetermined container and solidified by cooling to obtain a lipstick.

Example 24 was found to be a lipstick with an extremely light spread, with the score according to the use test in Example 12 being 4.2, and had a feeling of moistness.

Comparative Example 9 was found to have a slightly heavy spread, with the score being 2.0, and gave no feeling of moistness.

EXAMPLE 25

Rouge

| Talc | 30 |
| --- | --- |
| Mica | 25 |
| Titanium oxide | 3 |
| Titanium coated mica | 5.5 |
| Red color No. 202 | 0.5 |
| Spherical organic clay mineral *-1 | 20 |
| Sorbitan diisostearate | 1 |
| Squalene | 7 |
| Methylphenylpolysiloxane | 8 |

*-1 spherical organic clay mineral of No. 3 in Table 10

Preparation method

Pigments were mixed, and other components were added by melting with heating, followed by mixing and pulverization. The mixture was molded in a midplate to obtain a press-shaped rouge.

Example 25 was found to have an extremely good spread, finished without a powdery feeling, and moistness was felt on the cheek.

EXAMPLE 26

In 8 liters of water was dissolved 1 g of sodium hexametaphosphate, and 80 g of fine zinc oxide with an average particle size of 0.05 μm was dispersed therein. Further, 240 g of Laponite XLG was dispersed to prepare a gel. The gel obtained was spray dried by a disc spray dryer at a disc rotational number of 20,000 rpm, an inlet temperature of about 210° C., an exhaust temperature of about 110° C. to obtain 310 g of spherical powder of 2 to 20 μm.

It can be easily evaluated from electron microscope observation and EDX measurement (energy dispersion type analysis) attached thereto that the powder is spherical and zinc oxide is embedded uniformly internally thereof. That is, Figure shows a scanning electron microscope photograph of this powder, from which it was confirmed that the form was a truly spherical powder. When a spot analysis of the true spherical powder was conducted by an energy dispersion type X-ray analyzer, the existence of zinc was confirmed at all sites, and therefore, it was understood that zinc oxide is extremely uniformly dispersed in the spherical clay mineral.

By using the composite powder thus formed, an aerosol deodorant spray having the following composition was prepared.

| Components | % by weight |
| --- | --- |
| Freon 11 | 76.8 |
| Freon 12 | 19.2 |
| Composite powder | 1.2 |
| Talc | 1.8 |
| Isopropyl myristate | 0.5 |
| Tetra-2-ethylhexanoic acid diglycerolsorbitane | 0.5 |

The evaluation results of a deodorant over a lapse of time are shown below in Table 13. The effect of the deodorant of the present invention can be clearly seen.

TABLE 13

| Lapse of time | Site where test product is applied | Control side |
| --- | --- | --- |
| Before application | 1.8 | 1.5 |
| After 4 hours | 1.7 | 1.7 |
| After 24 hours | 1.2 | 1.8 |
| After 31 hours | 1.1 | 2.5 |

The test method is as described below.

Deodorizing test method

The test of the deodorant of the present invention was conducted by a panel of six healthy men aware of having an axillary odor. The test product was directly applied on only the axillary odor site once in the morning and in the afternoon every day for 2 days, a total of 4 times. The axillary odor site not applied with test product was called the control. Judgement was conducted according to the five judgement standards shown below, namely:

0: no axillary odor
1: slight axillary odor
2: clear axillary odor
3: axillary odor
4: very strong axillary odor.

COMPARATIVE EXAMPLE 10

In place of the composite powder used in Example 26, as powdery mixture obtained by simply mixing 0.3 g of fine zinc oxide and 0.9 g of Laponite XLG was used to prepare an aerosol deodorant spray in the same manner as in Example 25. The results of the deodorizing test conducted with the deodorant sprays of Example 26 and Comparative Example 10 are shown in Table 14. Thus, it can be understood that the composite powder of the present invention has a greater deodorant effect than when the respective components are individually formulated.

TABLE 14

| Lapse of time | Example 26 | Comparative Example 10 |
| --- | --- | --- |
| Before application | 2.0 | 1.8 |
| After 4 hours | 1.8 | 1.8 |
| After 24 hours | 1.1 | 1.9 |
| After 31 hours | 0.8 | 2.0 |

EXAMPLE 27

According to the same method as in Example 26, g of a composite powder was obtained from 80 g of Smecton SA (produced by Kunimine Kogyo Co.) and 20 g of fine zinc oxide. By using this composite powder, a deodorant powder having the following composition was prepared.

| Components | % by weight |
| --- | --- |
| Composite powder | 20.0 |
| Talc | 50.0 |
| Kaolin | 30.0 |

When an actual use test was practiced by use of the deodorant powder, after initiation of the test, in each panel, the axillary odor at the tested portion was reduced significantly at a rate of 5%, compared with the control portion. Further, the feeling during use was smooth.

We claim:

1. In a cosmetic composition selected from the group consisting of an eyeliner, mascara, powdery foundation, lipstick and rouge, and comprising at least one component selected from the group consisting of oil components, waxes, pigments, powders, surfactants, preservatives, dyes, antioxidants, perfumes, humectants, water-soluble polymers, oil-soluble polymers, and clay minerals, wherein the improvement comprises from 0.1% to 80% by weight of a spherical water-swellable clay mineral powder of hectorite or saponite having a specific surface area of at least 100 m$^2$/g and a particle size of 2 to 30 $\mu$m, whereby the composition exhibits improved smoothness, slippage and transparency.

2. A cosmetic composition according to claim 1, wherein the water-swellable clay mineral powder is obtained by dispersing a water-swellable clay mineral with a specific surface area of 100 m$^2$/g or more in an aqueous solvent, and then spray drying the dispersion.

3. In a cosmetic composition selected from the group consisting of an eyeliner, mascara, powdery foundation, lipstick and rouge, and comprising 0.05 to 75% by weight of at least one water-soluble substance selected from the group consisting of water soluble polymers, polyhydric alcohols and quaternary ammonium salts, wherein the improvement comprises a spherical organic composite clay mineral powder containing 25 to 99.5% of a water-swellable mineral clay powder of hectorite or saponite having a specific surface area of at least 100 m$^2$/g and a particle size of 2 to 30 $\mu$m, whereby the composition exhibits improved smoothness, slippage and transparency.

4. A cosmetic composition according to claim 3, wherein the spherical organic composite clay mineral powder is obtained by dispersing the water-swellable mineral clay with the specific surface area of 100 m$^2$/g or more and the water-soluble substance in an aqueous solvent, and then spray drying the dispersion.

5. In a cosmetic composition selected from the group consisting of an eyeliner, mascara, powdery foundation, lipstick and rouge, and comprising 0.05 to 75% by weight of at least one organic substance soluble in an organic solvent selected from the group consisting of oil components having an emollient effect, oil-soluble dyes and perfumes, wherein the improvement comprises 25 to 99.5% of a spherical organic composite clay mineral containing a water-swellable clay mineral powder of hectorite or saponite having a specific surface area of at least 100 $m^2/g$ and a particle size of 2 to 30 $\mu$m, whereby the composition exhibits improved smoothness, slippage and transparency.

6. A cosmetic composition according to claim 5, wherein the spherical organic composite clay mineral powder is obtained by dispersing the spherical water-swellable clay mineral powder obtained by spray drying an aqueous dispersion of the water-swellable clay mineral powder in an organic solvent containing the organic substance dissolved therein, and thereafter, volatilizing said organic solvent.

* * * * *

UNITED STATES PATENT AND TRADEMARK OFFICE
CERTIFICATE OF CORRECTION

PATENT NO. : 5,165,915
DATED : November 24, 1992
INVENTOR(S) : Tokubo et al.

It is certified that error appears in the above-identified patent and that said Letters Patent is hereby corrected as shown below:

Title Page   [22] Filed:  Delete " 19 " and substitute -- 14 --

Signed and Sealed this

Eighth Day of March, 1994

Attest:

BRUCE LEHMAN

Attesting Officer    Commissioner of Patents and Trademarks